(12) United States Patent
Polivka

(10) Patent No.: US 8,053,598 B2
(45) Date of Patent: Nov. 8, 2011

(54) COMPOUNDS, THEIR PREPARATION AND USE

(75) Inventor: Zdeněk Polivka, Prague (CZ)

(73) Assignee: High Point Pharmaceuticals, LLC, High Point, NC (US)

( * ) Notice: Subject to any disclaimer, the term of this patent is extended or adjusted under 35 U.S.C. 154(b) by 609 days.

(21) Appl. No.: 11/579,717

(22) PCT Filed: May 3, 2005

(86) PCT No.: PCT/EP2005/052013
§ 371 (c)(1),
(2), (4) Date: Sep. 11, 2008

(87) PCT Pub. No.: WO2005/105736
PCT Pub. Date: Nov. 10, 2005

(65) Prior Publication Data
US 2009/0012171 A1    Jan. 8, 2009

(30) Foreign Application Priority Data

May 5, 2004 (DK) .................. 2004 00718

(51) Int. Cl.
C07C 321/00 (2006.01)
A61K 31/19 (2006.01)
(52) U.S. Cl. ........................ 562/427; 514/569
(58) Field of Classification Search .................. None
See application file for complete search history.

(56) References Cited

U.S. PATENT DOCUMENTS

| | | | |
|---|---|---|---|
| 4,148,915 A | 4/1979 | Thuillier et al. | |
| 4,920,132 A | 4/1990 | Huang et al. | |
| 5,324,743 A | 6/1994 | Dillard et al. | |
| 5,773,469 A | 6/1998 | Kanojia et al. | |
| 5,919,793 A | 7/1999 | Brown et al. | |
| 6,448,293 B1 | 9/2002 | Andrews et al. | |
| 6,525,094 B1 | 2/2003 | Zhang et al. | |
| 6,555,577 B1 | 4/2003 | Mogensen et al. | |
| 6,569,901 B2 | 5/2003 | Mogensen et al. | |
| 6,630,504 B2 | 10/2003 | Andrews et al. | |
| 6,867,218 B2 | 3/2005 | Mogensen et al. | |
| 6,869,967 B2 | 3/2005 | Jeppesen et al. | |
| 6,869,975 B2 | 3/2005 | Abe et al. | |
| 6,875,780 B2 | 4/2005 | Auerbach et al. | |
| 6,972,294 B1 | 12/2005 | Murray et al. | |
| 7,091,245 B2 * | 8/2006 | Jeppesen et al. ............ 514/571 |
| 7,129,268 B2 | 10/2006 | Jeppesen et al. | |
| 7,202,213 B2 | 4/2007 | Mogensen et al. | |
| 7,709,528 B2 | 5/2010 | Jeppesen et al. | |
| 7,943,612 B2 | 5/2011 | Sauerberg | |
| 7,943,613 B2 | 5/2011 | Sauerberg et al. | |
| 2002/0115654 A1 | 8/2002 | Jeppesen et al. | |
| 2004/0024034 A1 | 2/2004 | Brooks et al. | |
| 2005/0080115 A1 | 4/2005 | Jeppesen et al. | |
| 2008/0114036 A1 | 5/2008 | Havranek et al. | |
| 2010/0197950 A1 | 8/2010 | Rasmussen et al. | |
| 2010/0210653 A1 | 8/2010 | Havranek et al. | |
| 2011/0039841 A1 | 2/2011 | Polivka et al. | |

FOREIGN PATENT DOCUMENTS

| | | |
|---|---|---|
| JP | 2003-171275 | 6/2003 |
| WO | 97/27847 | 8/1997 |
| WO | 97/27857 | 8/1997 |
| WO | 97/28115 | 8/1997 |
| WO | 97/28137 | 8/1997 |
| WO | 97/28149 | 8/1997 |
| WO | WO 97/43241 | 11/1997 |
| WO | WO 97/48674 | 12/1997 |
| WO | 98/27974 | 7/1998 |
| WO | 99/04815 | 2/1999 |
| WO | WO 99/20275 | 4/1999 |
| WO | WO 00/63153 | 10/2000 |
| WO | 01/00603 | 1/2001 |
| WO | 01/25181 | 4/2001 |
| WO | WO 01/25226 | 4/2001 |
| WO | WO 01/34137 | 5/2001 |
| WO | WO 01/34200 | 5/2001 |
| WO | WO 01/55085 | 8/2001 |
| WO | WO 01/55086 | 8/2001 |
| WO | WO 01/60807 | 8/2001 |
| WO | WO 01/66098 | 9/2001 |
| WO | 01/79197 | 10/2001 |
| WO | 02/14291 | 2/2002 |
| WO | WO 02/28434 | 4/2002 |
| WO | 02/46154 | 6/2002 |
| WO | WO 02/50048 | 6/2002 |
| WO | WO 2002/053547 | 7/2002 |
| WO | 02/059098 | 8/2002 |

(Continued)

OTHER PUBLICATIONS

Berger, J et al—The J of Biological Chem—1999—vol. 274—Part 10—pp. 6718-6725.
Leibowitz, M.D. et al—F E B S Lett—2000—vol. 473—pp. 333-336.
Oliver, W.R. et al—PNAS—2001—vol. 98—Part 9—pp. 5306-5311.
Muoio, D.M. et al—The J of Biological Chem—2002—vol. 277—Part 29—pp. 26089-26097.
Wang, Y-X et al—Cell—2003—vol. 113—pp. 159-170.
Luquet, S et al—FASEB J—2003—vol. 17—Part 13—pp. 209-226.
Tanaka, T et al—PNAS—2003—vol. 100—Part 26—pp. 15924-15929.
Holst, D et al—Biochem Biophys Acta—2003—vol. 1633—pp. 43-50.

(Continued)

Primary Examiner — Paul A Zucker
(74) Attorney, Agent, or Firm — Samuel B. Rollins; Robert S. Dailey

(57) ABSTRACT

Novel compounds of the general formula (I), the use of these compounds as pharmaceutical compositions, pharmaceutical compositions comprising the compounds and methods of treatment employing these compounds and compositions. The present compounds may be useful in the treatment and/or prevention of conditions mediated by Peroxisome Proliferator-Activated Receptors (PPAR), in particular the PPARδ subtype.

49 Claims, No Drawings

FOREIGN PATENT DOCUMENTS

| | | |
|---|---|---|
| WO | WO 2002/062774 | 8/2002 |
| WO | WO 2002/070011 | 9/2002 |
| WO | 02/076957 | 10/2002 |
| WO | 02/079162 | 10/2002 |
| WO | 02/080899 | 10/2002 |
| WO | 02/098840 | 12/2002 |
| WO | 02/100812 | 12/2002 |
| WO | WO 2003/002081 | 1/2003 |
| WO | 03/016265 | 2/2003 |
| WO | 03/016291 | 2/2003 |
| WO | WO 2003/011807 | 2/2003 |
| WO | WO 2003/011814 | 2/2003 |
| WO | WO 2003/02395 | 3/2003 |
| WO | 03/033493 | 4/2003 |
| WO | 03/035603 | 5/2003 |
| WO | 03/072100 | 9/2003 |
| WO | 03/074050 | 9/2003 |
| WO | 03/074051 | 9/2003 |
| WO | 03/074052 | 9/2003 |
| WO | WO 2003/074495 | 9/2003 |
| WO | 03/084916 | 10/2003 |
| WO | 03/097607 | 11/2003 |
| WO | WO 2004/000315 | 12/2003 |
| WO | WO 2004/000762 | 12/2003 |
| WO | 2004/005253 | 1/2004 |
| WO | WO 2004/007439 | 1/2004 |
| WO | 2004/022533 | 3/2004 |
| WO | WO 2004/037775 | 5/2004 |
| WO | WO 2004/037776 | 5/2004 |
| WO | WO 2004/060871 | 7/2004 |
| WO | WO 2004/063165 | 7/2004 |
| WO | WO 2004/063166 | 7/2004 |
| WO | WO 2004/073606 | 9/2004 |
| WO | WO 2004/080943 | 9/2004 |
| WO | WO 2004/080947 | 9/2004 |
| WO | WO 2004/092117 | 10/2004 |
| WO | WO 2004/093879 | 11/2004 |
| WO | WO 2004/099170 | 11/2004 |
| WO | WO 2005/054176 | 6/2005 |
| WO | WO 2005/097098 | 10/2005 |
| WO | WO 2005/097762 | 10/2005 |
| WO | WO 2005/097763 | 10/2005 |
| WO | WO 2005/105725 | 11/2005 |
| WO | WO 2005/105735 | 11/2005 |
| WO | WO 2007/071766 | 6/2007 |
| WO | WO 2007/101864 | 9/2007 |
| WO | WO 2007/141295 | 12/2007 |

OTHER PUBLICATIONS

Dressel, U et al—Mol Endocrinol—2003—vol. 17—Part 12—pp. 2477-2493.
Lee, C-H et al—Science—2003—vol. 32—pp. 453-457.
Berger et al., "Physiological and Therapeutic Roles of Peroxisome Proliferator-Activated Receptors,", Diabetes Technology & Therapeutics, 4(2);163-174 (2002).
Chilonczyk et al., "Hypolipidaemic and antiplatelet agents", Expert Opin. Ther. Patents, 11(8):1301-1327 (2001).
Colagiuri et al. American Journal of Public Health, 96(9):1562-1569 (2006).
Curtis et al., The Journal of the American Board of Family Practice, 18:37-43 (2005).
Epple et al. Bioorganic & Medicinal Chemistry Letters, 16:4376-4380 (2006).
Everett et al., "The role of hepatic peroxisome proliferator-activated receptors (PPARs) in health and disease," Liver, 20:191-199 (2000).
Fruchart, "PPAR and Cardiovascular Risk: Overview," J. Cardiovasc. Risk, 8(4):185-186 (2001).
Golub et al., Science, 286:531-537 (1999).
Gross et al., Best Practice & Research Clinical Endocrinology & Metabolism, 21:687-710 (2007).
Havranek et al., "E/Z Isomerization of 3,3-disubstituted allylic thioethers" Tetrahedron Lett., vol. 48, pp. 6970-6973 (2007).
Hussain et al., Diabetes Research and Clinical Practice, 76:317-326 (2007).
International Preliminary Report on Patentability and Written Opinion for Application No. PCT/EP2005/052013, mailed Nov. 7, 2006.
International Search Report and Written Opinion of the ISR, PCT/EP2005/052013 dated Nov. 16, 2006.
Jones, "Peroxisome Proliferative-Activated Receptor (PPAR) Modulators: Diabetes and Beyond," Medicinal Research Reviews, 21(6):540-552 (2001).
Kaplan et al., "PPARs, Insulin Resistance and Type 2 Diabetes," J. Cardiovasc. Risk, vol. 8(4), pp. 211-217 (Aug. 2001)
Kersten et al., "Roles of PPARs in health and disease," Nature, vol. 405, pp. 421-424 (May 2000).
Landreth et al., Neurobiology of Aging, 22:937-944 (2001).
Lee et al., "PPAR-delta regulates glucose metabolism and insulin sensitivity", Proceedings of the National Academy of Sciences of the USA, 103(9):3444-3449 (2006).
Liu et al., "Identification of a Series of PPAR gamma/delta Dual Agonists via Solid-Phase Parallel.Synthesis," Bioorg. Med. Chem. Lett., 11:2959-2962 (2001).
Michalik et al., "Peroxisome proliferator-activated receptors: three isotypes for a multitude of functions," Curr. Opin. Biotechnology, 10:564-570 (1999).
Miller et al., "Novel peroxisome proliferator-activated receptor ligands for type 2 diabetes and the metabolic syndrome," Expert Opin. Investig. Drugs, 12(9):1489-1500 (2003).
Mital, "PPARs: Nuclear Receptors for Antidiabetics," Crips, 3(1):5-8 (2002).
Park, Diabetes Research and Clinical Practice 66S, S33-S35 (2004).
Pending Claims for U.S. Appl. No. 11/579,716, dated Nov. 17, 2010.
Pending Claims for U.S. Appl. No. 12/689,014 dated Feb. 11, 2011.
Pending Claims for U.S. Appl. No. 13/079,460 dated Apr. 4, 2011.
Peters et al., Biochimica et Biophysica Acta 2009, 1796, 230-241.
Sauerberg et al., Identification and Synthesis of a Novel Selective Partial PPAR-delta Agonist with Full Efficacy on Lipid Metabolism In Vitro and In Vivo J. Med. Chem., 50:1495-1503 (2007).
Schiffrin et al., "Peroxisome Proliferator-Activated Receptors: Vascular and Cardiac Effects in Hypertension", Hypertension, 42:664-668 (2003).
Tiikkainen et al., "Effects of Rosiglitazone and Metformin on Liver Fat Content, Hepatic Insulin.Resistance, Insulin Clearance, and Gene Expression in Adipose Tissue in Patients with Type 2 Diabetes," Diabetes, 53:2169-2176 (2004).
Torra et al., "Peroxisome proliferator-activated receptors: from transcriptional control to clinical practice," Curr. Opin. Lipidol., 12:245-254 (2001).
Vamecq et al.., "Medical significance of peroxisome proliferator-activated receptors," The Lancet, 354:141-148 (1999).
Wahli, "Peroxisome Proliferator-Activated Receptors (PPARs): from metabolic control to epidermal.wound healing," Swiss Med. Weekly, 132:83-91 (2002).
Wilson et al., "The PPARs: From Orphan Receptors to Drug Discovery" J. Med. Chem., 43(4):527-550 (2000).

* cited by examiner

COMPOUNDS, THEIR PREPARATION AND USE

CROSS-REFERENCE TO RELATED APPLICATIONS

This application is a 35 U.S.C. §371 National Stage application of International Application PCT/EP2005/052013, filed May 3, 2005, which claimed priority of Danish Patent Application PA 2004 00718, filed May 5, 2004; this application claims priority under 35 U.S.C. §119(e) of U.S. Provisional Application 60/570,698, filed May 14, 2004.

FIELD OF THE INVENTION

The present invention relates to novel compounds, to the use of these compounds as pharmaceutical compositions, to pharmaceutical compositions comprising the compounds and to a method of treatment employing these compounds and compositions. More specifically, the compounds of the invention can be utilised in the treatment and/or prevention of conditions mediated by the Peroxisome Proliferator-Activated Receptors (PPAR), in particular the PPARδ subtype.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty add β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., *J. Biol. Chem.*, 1999, Vol 274, pp. 6718-6725). Later it has been shown that PPARδ activation leads to increased levels of HDL cholesterol in db/db mice (Leibowitz et al. FEBS letters 2000, 473, 333-336). Further, a PPARδ agonist when dosed to insulin-resistant middle-aged obese rhesus monkeys caused a dramatic dose-dependent rise in serum HDL cholesterol while lowering the levels of small dense LDL, fasting triglycerides and fasting insulin (Oliver et al. PNAS 2001, 98, 5306-5311). The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARα knockout mice. Muoio et al. (J. Biol. Chem. 2002, 277, 26089-26097) showed that the high levels of PPARδ in skeletal muscle can compensate for deficiency in PPARα.

Recently, two different transgenic mouse models over-expressing PPARδ in either adipose tissue (*Cell* 2003, 113, 159-170) or in muscle tissue (*FASEB J* 2003, 17, 209-226) have both shown up-regulation of genes (LPL, FABP, FAT, CD36, CPT1b, and ACS) and proteins (UCP-2) responsible for lipid uptake and metabolism and energy uncoupling. Both types of mice had reduced adipose tissue and were protected against high fat diet induced body weight gain. Further, pharmacological treatment of both high fat diet induced insulin resistant mice and diabetic ob/ob with the potent PPARδ agonist GW501516 showed lowering of plasma glucose and insulin and improved insulin sensitivity (*PNAS* 2003, 100, 15924-15929). In vivo increased oxygen consumption suggesting fuel-switch from glucose to FFA, as well as FFA oxidation In skeletal muscle was demonstrated both in vivo and in vitro. Supportive for the hypothesis of skeletal muscle being the major target organ were two publications on In vitro treatment of C2C12 muscle cells with GW501516 showing regulation of genes involved with TG hydrolysis and FFA oxidation (LPL↑, ACS4↑, CTP1↑), preferential lipid utilization (PDK4↑), energy expenditure (UCP1↑, -2↑, -3↑) and lipid efflux (ABCA1/G1↑) (*BioChem. Biophys. Acta* 2003, 1633, 43-50; *Mol. Endocrin.* 2003, 17, 2477-2493). Direct and an indirect mechanisms recently demonstrated prompted the authors to suggest that "PPARδ and its ligands may serve as therapeutic targets to attenuate inflammation and slow the progression of atherosclerosis" (*Science* 2003, 302, 453-457).

Taken together these observations suggest that PPARδ activation is useful in the treatment and prevention of cardiovascular diseases and conditions including atherosclerosis, hypertriglyceridemia, and mixed dyslipidaemia as well as type 2 diabetes.

A number of PPARδ compounds have been reported to be useful in the treatment of hyperglycemia, hyperlipidemia and hypercholesterolemia (WO 01/00603, WO 02/59098, WO 03/084916, WO 03/074050, WO 03/074051, WO 03/074052, WO 03/035603, WO 03/97607, WO 04/005253, WO 03/33493, WO 03/16291, WO 02/76957, 02/46154, WO 03/16265, WO 02/100812, WO 02/98840, WO 02/80899, WO 02/79162, WO 03/072100, WO 01/25181, WO 02/14291, WO 01/79197, WO 99/4815, WO 97/28149, WO 98/27974, WO 97/28115, WO 97/27857, WO 97/28137, WO 97/27847).

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

Definitions

In the structural formulas given herein and throughout the present specification the following terms have the indicated meaning:

The term "$C_{1-6}$-alkyl" as used herein, alone or in combination, represent a linear or branched, saturated hydrocarbon chain having the indicated number of carbon atoms. Representative examples include, but are not limited to methyl, ethyl, n-propyl, isopropyl, butyl, isobutyl, sec-butyl, tert-butyl, pentyl, isopentyl, hexyl, isohexyl and the like.

The term "$C_{1-6}$-alkylcarbonyl" as used herein, represents a "$C_{1-6}$-alkyl" group as defined above having the indicated number of carbon atoms linked through a carbonyl group. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" as used herein refers to a monovalent substituent comprising a "$C_{1-6}$-alkyl" group as defined above linked through a sulfonyl group. Representative examples include, but are not limited to, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

The term "$C_{1-6}$-alkylamido" as used herein, refers to an acyl group linked through an amino group; Representative examples include, but are not limited to acetylamino, propionylamino, butyrylamino, isobutyrylamino, pivaloylamino, valerylamino and the like.

The term "$C_{3-6}$-cycloalkyl" as used herein, alone or in combination, represent a saturated monocyclic hydrocarbon group having the indicated number of carbon atoms. Representative examples include, but are not limited to cyclopropyl, cyclobutyl, cyclopentyl, cyclohexyl and the like.

The term "$C_{2-6}$-alkenyl" as used herein, represent an olefinically unsaturated branched or straight hydrocarbon group having from 2 to the specified number of carbon atoms and at least one double bond. Representative examples include, but are not limited to, vinyl, 1-propenyl, 2-propenyl, allyl, isopropenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Representative examples include, but are not limited to, 1-propynyl, 2-propynyl, 1-butynyl, 2-butynyl, 1-pentynyl, 2-pentynyl and the like.

The term "$C_{4-6}$-alkenynyl" as used herein, represent an unsaturated branched or straight hydrocarbon group having from 4 to the specified number of carbon atoms and both at least one double bond and at least one triple bond. Representative examples include, but are not limited to, 1-penten-4-ynyl, 3-penten-1-ynyl, 1,3-hexadiene-5-ynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$C_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a "$C_{1-6}$-alkyl" group as defined above linked through a divalent sulfur atom having its free valence bond from the sulfur atom and having 1 to 6 carbon atoms. Representative examples include, but are not limited to, methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Examples of cycloalkoxy groups are cyclopropylthio, cyclobutylthio, cyclopentylthio, cyclohexylthio and the like.

The term "$C_{1-6}$-alkylamino" as used herein, alone or in combination, refers to a straight or branched monovalent substituent comprising a "$C_{1-6}$-alkyl" group as defined above linked through amino having a free valence bond from the nitrogen atom. Representative examples include, but are not limited to, methylamino, ethylamino, propylamino, butylamino, pentylamino and the like.

The term "$C_{1-6}$-alkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylamino-carbonyl, 4-methylpentylaminocarbonyl, neopentylaminocarbonyl, n-hexylaminocarbonyl and 2-2-dimethylpropylaminocarbonyl and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom. Representative examples include, but are not limited to, cyclopropylamino, cyclobutylamino, cyclopentylamino, cyclohexylamino and the like.

The term "$C_{1-6}$-alkoxy$C_{1-6}$-alkyl" as used herein, alone or in combination, refers to a "$C_{1-6}$-alkyl" group as defined above whereto is attached a "$C_{1-6}$-alkoxy" group as defined above. Representative examples include, but are not limited to, methoxymethyl, ethoxymethyl, methoxyethyl, ethoxyethyl and the like.

The term "aryl" as used herein refers to an aromatic monocyclic or an aromatic fused bi- or tricyclic hydrocarbon group. Representative examples include, but are not limited to, phenyl, naphthyl, anthracenyl, phenanthrenyl, azulenyl, fluorenyl, indenyl, pentalenyl and the like.

The term "arylene" as used herein refers to divalent aromatic monocyclic or a divalent aromatic fused bi- or tricyclic hydrocarbon group. Representative examples include, but are not limited to, phenylene, naphthylene and the like.

The term "arylcarbonyl" as used herein represents an "aryl" group as defined above linked through a carbonyl group. Representative examples include, but are not limited to, phenylcarbonyl, naphthylcarbonyl, anthracenylcarbonyl, phenanthrenylcarbonyl, azulenylcarbonyl and the like The term "arylsulfonyl" as used herein refers to an "aryl" group as defined above linked through a sulfonyl group. Representative examples include, but are not limited to, phenylsulfonyl, naphthylsulfonyl, anthracenylsulfonyl, phenanthrenylsulfonyl, azulenylsulfonyl, and the like.

The term "arylsulfonyloxy" as used herein refers to a as used herein refers to an arylsulfonyl group as defined herein linked to an oxygen atom having its free valence bond from the oxygen atom. Representative examples include, but are not limited to phenylsulfonyloxy, naphthylsulfonyloxy, anthracenylsulfonyloxy, phenanthrenylsulfonyloxy, azulenylsulfonyloxy and the like.

The term "$C_{1-6}$-alkylsulfonyloxy" as used herein refers to a $C_{1-6}$-alkylsulfonyl group as defined herein linked to an oxygen atom having its free valence bond from the oxygen atom. Representative examples include, but are not limited to methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, neopentylsulfonyloxy, tert-pentylsulfonyloxy, n-hexylsulfonyloxy, isohexylsulfonyloxy and the like.

The term "arylamido" as used herein refers to an arylcarbonyl group linked through an amino group. Representative examples include, but are not limited to phenylcarbonylamino, naphthylcarbonylamino, anthracenylcarbonylamino, phenanthrenylcarbonylamino, azulenylcarbonylamino and the like.

The term "aryl$C_{2-6}$-alkynyl" as used herein refers to an "aryl" group as defined above attached to a "$C_{2-6}$-alkynyl" group as defined above. Representative examples include, but are not limited to phenylpropynyl, naphthylbutynyl, anthracenylpentynyl, phenanthrenylhexynyl, azulenylpropynyl, fluorenylallyl, indenylbutynyl, pentalenylhexynyl and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms. Representative examples include, but are not limited to, dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a "$C_{1-6}$-alkyl" group as defined above linked through a carbonyl group. Representative examples include, but are not limited to, acetyl, propionyl, butyryl, isobutyryl, pivaloyl, valeryl and the like.

The term "heteroaryl" as used herein, alone or in combination, refers to a monovalent substituent comprising a 5-7 membered monocyclic aromatic system or a 8-10 membered bicyclic aromatic system containing one or more heteroatoms selected from nitrogen, oxygen and sulfur, e.g. furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, isoindolyl, indolyl, benzimidazolyl, benzoxazolyl, benzothiazolyl, benzofuranyl, tetrazolyl, carbazolyl, benzothienyl, pteridinyl and purinyl and the like.

The term "heteroarylene" as used herein, alone or in combination, refers to divalent 5-7 membered monocyclic aromatic system or a 8-10 membered bicyclic aromatic system containing one or more heteroatoms selected from nitrogen, oxygen and sulfur, e.g. furylene, thienylene, pyrrolylene, imidazolylene, pyrazolylene, triazolylene, pyrazinylene, pyrimidin-ylene, pyridazinylene, isothiazolylene, isoxazolylene, oxazolylene, oxadiazolylene, thiadiazolylene, quinolylene, isoquinolylene, quinazolinylene, quinoxalinnylene, indolylene, benzimidazolylene, benzofuranylene, benzothienylene, pteridinylene and purinylene and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltloxy, benzimidazolyloxy, benzofuranyloxy, pteridinyloxy and purinyloxy and the like.

The term "aralkyl" as used herein refers to a straight or branched saturated carbon chain containing from 1 to 6 carbons substituted with an aromatic carbohydride. Representative examples include, but are not limited to, benzyl, phenethyl, 3-phenylpropyl, 1-naphthylmethyl, 2-(1-naphthyl) ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl) methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom. Representative examples include, but are not limited to, (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "heteroaryl$C_{2-6}$-alkynyl" as used herein refers to a "heteroaryl" as defined herein attached to a "$C_{2-6}$-alkynyl" group as defined above. Representative examples include, but are not limited to furylpropynyl, thienylbutynyl, pyrrolylpentynyl, imidazolylpropynyl, pyrazolylbutynyl, triazolylpentynyl, pyridylhexynyl, pyrazinylhexynyl, pyrimidinylpropynyl, pyridazinylbutynyl, isothiazolylpentynyl, isoxazolylhexynyl, oxazolylpropynyl, oxadiazolylbutynyl, thiadiazolylpentynyl, quinolylhexynyl, isoquinolylpropynyl, quinazolinylbutynyl, quinoxalinnylpentynyl, isoindolylhexynyl, indolylpropynyl, benzimidazolylbutynyl, benzoxazolylpentynyl, benzothiazolylallyl, benzofuranylhexynyl, tetrazolylpropynyl, carbazolylbutynyl, benzothienylpentynyl, pteridinylallyl, purinylhexynyl and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy. Representative examples include, but are not limited to, phenylthio, (4-methylphenyl)-thio, (2-chlorophenyl)thio and the like.

The term "live to eight member ring" as used herein refers to a saturated or unsaturated, substituted or unsubstituted hydrocarbon chain or hydrocarbon-heteroatom chain having from 3 to 6 atoms together with the carbon atom in Ar, to which they are attached, and the adjacent carbon atom form a five to eight member ring.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "treatment" is defined as the management and care of a patient for the purpose of combating or alleviating the disease, condition or disorder, and the term includes the administration of the active compound to prevent the onset of the symptoms or complications, or alleviating the symptoms or complications, or eliminating the disease, condition, or disorder.

The term "pharmaceutically acceptable" is defined as being suitable for administration to humans without adverse events.

DESCRIPTION OF THE INVENTION

The present invention relates to compounds of the general formula (I):

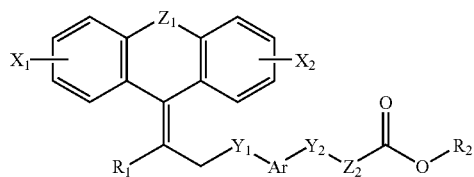

(I)

wherein $X_1$ is hydrogen, halogen, hydroxy, cyano, or amino; or $X_1$ is $C_{1-6}$-alkyl, $C_{3-6}$-cycloalkyl, $C_{2-6}$-alkenyl, $C_{2-6}$-alkynyl, aralkyl, heteroaralkyl, aryl$C_{2-6}$-alkynyl, heteroaryl$C_{2-6}$-alkynyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; or $X_1$ is aryl or heteroaryl each of which is optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; and $X_2$ is hydrogen, halogen, hydroxy, cyano, or amino; or $X_2$ is $C_{1-6}$-alkyl, $C_{3-6}$-cycloalkyl, $C_{2-6}$-alkenyl, $C_{2-6}$-alkynyl, aralkyl, heteroaralkyl, aryl$C_{2-6}$-alkynyl, heteroaryl$C_{2-6}$-alkynyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; or $X_2$ is aryl or heteroaryl each of which is optionally substituted with one or more substituents selected from halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; and Ar is arylene which is optionally substituted with one or more substituents selected from halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or two of the substituents when placed in adjacent positions together with the atoms to which they are attached my form a five to eight member ring; and $Y_1$ is O or S; and $Y_2$ is O or S; and $Z_1$ is —$(CH_2)_n$— wherein n is 0, 1, 2 or 3; and $Z_2$ is —$(CH_2)_m$— wherein m is 1, 2 or 3; and $R_1$ is hydrogen, halogen or a substituent selected from $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and $R_2$ is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein $X_1$ is halogen or cyano.

In one embodiment, the present invention is concerned with compounds of formula (I) wherein $X_1$ is halogen.

In another embodiment, the present invention is concerned with compounds of formula (I) wherein $X_1$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens.

In another embodiment, the present invention is concerned with compounds of formula (I) wherein $X_1$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, arylcarbonyl, $C_{1-6}$-alkylsulfonyl, $C_{1-6}$-alkylsulfonyloxy, arylsulfonyl, arylsulfonyloxy each of which is optionally substituted with one or more halogens.

In another embodiment, the present invention is concerned with compounds of formula (I) wherein $X_1$ is $C_{1-6}$-alkyl, aralkyl, heteroaralkyl, $C_{1-6}$-alkoxy, $C_{3-6}$-cycloalkoxy, aryloxy, aralkoxy, heteroaralkoxy, each of which is optionally substituted with one or more halogens.

In another embodiment, the present invention is concerned with compounds of formula (I) wherein $X_1$ is $C_{1-6}$-alkyl or $C_{1-6}$-alkoxy, each of which is optionally substituted with one or more halogens.

In another embodiment, the present invention is concerned with compounds of formula (I) wherein $X_1$ is $C_{1-6}$-alkyl.

In another embodiment, the present invention is concerned with compounds of formula (I) wherein $X_1$ is aryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is aryl optionally substituted with one or more substituents selected from
  halogen; or
  $C_{1-6}$-alkyl optionally substituted with one or more halogens.

In another embodiment, the present invention is concerned with compounds of formula (I) wherein $X_1$ is aryl optionally substituted with one or more halogens.

In another embodiment, the present invention is concerned with compounds of formula (I) wherein $X_1$ is phenyl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is phenyl optionally substituted with one or more substituents selected from
  halogen; or
  $C_{1-6}$-alkyl optionally substituted with one or more halogens.

In another embodiment, the present invention is concerned with compounds of formula (I) wherein $X_1$ is phenyl optionally substituted with one or more halogens.

In another embodiment, the present invention is concerned with compounds of formula (I) wherein $X_1$ is phenyl.

In another embodiment, the present invention is concerned with compounds of formula (I) wherein $X_1$ is heteroaryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_1$ is heteroaryl optionally substituted with one or more substituents selected from
  halogen; or
  $C_{1-6}$-alkyl optionally substituted with one or more halogens.

In another embodiment, the present invention is concerned with compounds of formula (I) wherein $X_1$ is heteroaryl optionally substituted with one or more halogens.

In another embodiment, the present invention is concerned with compounds of formula (I) wherein $X_1$ is furyl or thienyl optionally substituted with one or more halogens.

In another embodiment, the present invention is concerned with compounds of formula (I) wherein $X_2$ is halogen or cyano.

In another embodiment, the present invention is concerned with compounds of formula (I) wherein $X_2$ is halogen.

In another embodiment, the present invention is concerned with compounds of formula (I) wherein $X_2$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens.

In another embodiment, the present invention is concerned with compounds of formula (I) wherein $X_2$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, arylcarbonyl, $C_{1-6}$-alkylsulfonyl, $C_{1-6}$-alkylsulfonyloxy, arylsulfonyl, arylsulfonyloxy each of which is optionally substituted with one or more halogens.

In another embodiment, the present invention is concerned with compounds of formula (I) wherein $X_2$ is $C_{1-6}$-alkyl, aralkyl, heteroaralkyl, $C_{1-6}$-alkoxy, $C_{3-6}$-cycloalkoxy, aryloxy, aralkoxy, heteroaralkoxy, each of which is optionally substituted with one or more halogens.

In another embodiment, the present invention is concerned with compounds of formula (I) wherein $X_2$ is $C_{1-6}$-alkyl or $C_{1-6}$-alkoxy, each of which is optionally substituted with one or more halogens.

In another embodiment, the present invention is concerned with compounds of formula (I) wherein $X_2$ is $C_{1-6}$-alkyl.

In another embodiment, the present invention is concerned with compounds of formula (I) wherein $X_2$ is aryl optionally substituted with one or more substituents selected from
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is aryl optionally substituted with one or more substituents selected from
halogen; or
$C_{1-6}$-alkyl optionally substituted with one or more halogens.

In another embodiment, the present invention is concerned with compounds of formula (I) wherein $X_2$ is aryl optionally substituted with one or more halogens.

In another embodiment, the present invention is concerned with compounds of formula (I) wherein $X_2$ is phenyl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is phenyl optionally substituted with one or more substituents selected from
halogen; or
$C_{1-6}$-alkyl optionally substituted with one or more halogens.

In another embodiment, the present invention is concerned with compounds of formula (I) wherein $X_2$ is phenyl optionally substituted with one or more halogens.

In another embodiment, the present invention is concerned with compounds of formula (I) wherein $X_2$ is phenyl.

In another embodiment, the present invention is concerned with compounds of formula (I) wherein $X_2$ is heteroaryl optionally substituted with one or more substituents selected from
halogen; or
$C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

In another embodiment, the present invention is concerned with compounds of formula (I) wherein $X_2$ is heteroaryl optionally substituted with one or more substituents selected from
halogen; or
$C_{1-6}$-alkyl optionally substituted with one or more halogens.

In another embodiment, the present invention is concerned with compounds of formula (I) wherein $X_2$ is heteroaryl optionally substituted with one or more halogens.

In another embodiment, the present invention is concerned with compounds of formula (I) wherein $X_2$ is furyl or thienyl optionally substituted with one or more halogens.

In another embodiment, the present invention is concerned with compounds of formula (I) wherein Ar is phenylene which is optionally substituted with one or more substituents selected from
halogen, hydroxy or cyano; or
$C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or
two of the substituents when placed in adjacent positions together with the atoms to which they are attached my form a five to eight member ring.

In another embodiment, the present invention is concerned with compounds of formula (I) wherein Ar is phenylene which is optionally substituted with one or more substituents selected from
halogen; or
$C_{1-6}$-alkyl, $C_{1-6}$-alkoxy, aryloxy or aralkoxy each of which is optionally substituted with one or more halogens; or
two of the substituents when placed in adjacent positions together with the atoms to which they are attached form a five membered ring.

In another embodiment, the present invention is concerned with compounds of formula (I) wherein Ar is phenylene which is optionally substituted with methyl.

In another embodiment, the present invention is concerned with compounds of formula (I) wherein Ar is phenylene.

In another embodiment, the present invention is concerned with compounds of formula (I) wherein $Y_1$ is S.

In another embodiment, the present invention is concerned with compounds of formula (I) wherein $Y_1$ is O.

In another embodiment, the present invention is concerned with compounds of formula (I) wherein $Y_2$ is O.

In another embodiment, the present invention is concerned with compounds of formula (I) wherein $Y_2$ is S.

In another embodiment, the present invention is concerned with compounds of formula (I) wherein n is 1 or 2.

In another embodiment, the present invention is concerned with compounds of formula (I) wherein n is 1.

In another embodiment, the present invention is concerned with compounds of formula (I) wherein n is 2.

In another embodiment, the present invention is concerned with compounds of formula (I) wherein m is 1.

In another embodiment, the present invention is concerned with compounds of formula (I) wherein $R_1$ is hydrogen or a substituent selected from
$C_{1-6}$-alkyl, aralkyl, $C_{1-6}$-alkoxy, aryloxy, aralkoxy each of which is optionally substituted with one or more halogens.

In another embodiment, the present invention is concerned with compounds of formula (I) wherein $R_1$ is hydrogen or a substituent selected from
$C_{1-6}$-alkyl, $C_{1-6}$-alkoxy each of which is optionally substituted with one or more halogens.

In another embodiment, the present invention is concerned with compounds of formula (I) wherein $R_1$ is hydrogen.

In another embodiment, the present invention is concerned with compounds of formula (I) wherein $R_2$ is hydrogen.

In another embodiment, the present invention is concerned with compounds of formula I wherein alkyl is methyl or ethyl.

In another embodiment, the present invention is concerned with compounds of formula I wherein alkenyl is vinyl or 1-propenyl.

In another embodiment, the present invention is concerned with compounds of formula I wherein alkynyl is 1-propynyl.

In another embodiment, the present invention is concerned with compounds of formula I wherein alkenynyl is 1-pentene-4-yne.

In another embodiment, the present invention is concerned with compounds of formula I wherein alkoxy is methoxy, ethoxy, isopropoxy or cyclopropoxy.

In another embodiment, the present invention is concerned with compounds of formula I wherein aryl is phenyl.

In another embodiment, the present invention is concerned with compounds of formula I wherein arylene is phenylene.

In another embodiment, the present invention is concerned with compounds of formula I wherein halogen is bromine, fluorine or chlorine.

In another embodiment, the present invention is concerned with compounds of formula I wherein perhalomethyl is trifluoromethyl.

In another embodiment, the present invention is concerned with compounds of formula I wherein perhalomethoxy is trifluoromethoxy.

In another embodiment, the present invention is concerned with compounds of formula I wherein heteroaryl is furyl or thienyl.

In another embodiment, the present invention is concerned with compounds of formula I wherein aralkyl is benzyl.

In another embodiment, the present invention is concerned with compounds of formula I wherein aryloxy is phenoxy.

In another embodiment, the present invention is concerned with compounds of formula I wherein aralkoxy is benzyloxy.

In another embodiment, the present invention is concerned with compounds of formula I which are PPARδ agonists.

In another embodiment, the present invention is concerned with compounds of formula I which are selective PPARδ agonists.

Examples of specific compounds of the invention are:
{4-[2-(2-Bromo-10,11-dihydro-dibenzo[a,d]cyclohepten-5-ylidene)-ethylsulfanyl]-2-methylphenoxy}-acetic acid;
{4-[2-(2-Phenyl-10,11-dihydro-dibenzo[a,d]cyclohepten-5-ylidene)-ethylsulfanyl]-2-methylphenoxy}-acetic acid; or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be pre-pared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

In another aspect, the present invention relates to a method of treating and/or preventing Type I or Type II diabetes.

In a still further aspect, the present invention relates to the use of one or more compounds of the general formula I or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, artherosclerosis, hyperlipidemia, coronary artery disease, myocardial ischemia and other cardiovascular disorders.

In still another aspect, the present compounds are useful for the treatment and/or prophylaxis of diseases or complications related to atherosclerosis such as coronary artery diseases, coronary heart diseases, heart attack, myocardial infarct, coronary infarct, transient ischemic attack (TIA) or stroke.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

In yet another aspect, the invention also relates to the use of the present compounds, which after administration lower the bio-markers of atherosclerosis like, but not limited to, c-reactive protein (CRP), TNFα and IL-6.

The present compounds may also be administered in combination with one or more further pharmacologically active substances e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-518674, LY-519818, MK-767, atorvastatin, fluvastatin, lovastatin, pravastatin, simvastatin, cerivastin, acipimox, ezetimibe, probucol, dextrothyroxine or nicotinic acid.

In yet another embodiment the present compounds are administered in combination with a thiazolidinedione e.g. troglitazone, ciglitazone, pioglitazone or rosiglitazone.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

EXAMPLES

The following examples and general procedures refer to intermediate compounds and final products identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed nuclear magnetic resonance (NMR). NMR shifts (δ) are given in parts per million (ppm. Mp is melting point and is given in ° C.

The abbreviations as used in the examples have the following meaning:
THF: tetrahydrofuran
DMSO: dimethylsulfoxide
$CDCl_3$: deutorated chloroform
DMF: N,N-dimethylformamide
min: minutes
h: hours General Procedure (A)
Step A:
Reacting a compound of formula II (J. Med. Chem 2002, 45, 789 and references therein)

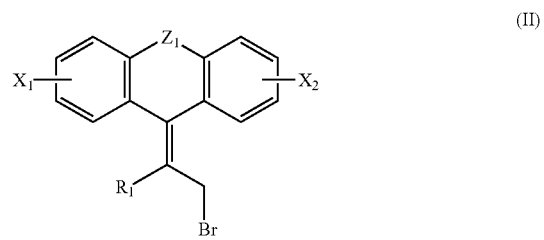

wherein $R_1$ and $Z_1$ are defined as above, and at least one of $X_1$ and $X_2$ is bromine and the other is hydrogen, with boronic acids or tributylstanane derivatives of $X_1$ and $X_2$, wherein $X_1$ and $X_2$ are aryl and heteroaryl as defined above, to give the desired substituted tricyclic intermediate.

Step B:
Reacting a compound of formula II, wherein $X_1$, $X_2$, $R_1$ and $Z_1$ are defined as above, with a compound of formula III

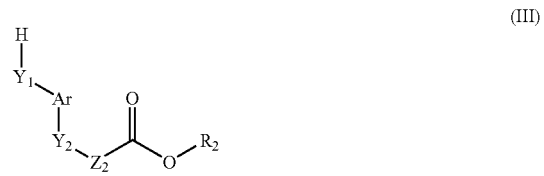

wherein $Y_1$, Ar, $Y_2$, $Z_2$ and $R_2$ are defined as above, except that R is not hydrogen, under alkylating conditions, using $K_2CO_3$/acetone and the like, to obtain a compound of formula I, wherein $X_1$, $X_2$, $Y_1$, $Y_2$, Ar $Z_1$, $Z_2$, $R_1$ and $R_2$ are defined as above, except that $R_2$ is not hydrogen.

General Procedure (B)
Step A:
By chemical or enzymatic saponification of a compound of formula I, wherein $X_1$, $X_2$, $Y_1$, $Y_2$, Ar, $Z_1$, $Z_2$, $R_1$ and $R_2$ are defined as above, except that $R_2$ is not hydrogen to give a compound of formula I, wherein $X_1$, $X_2$, $Y_1$, $Y_2$, Ar, $Z_1$, $Z_2$, $R_1$ and $R_2$ are defined as above, except that $R_2$ is hydrogen.

Example 1

{4-[2-(2-Bromo-10,11-dihydro-dibenzo[a,d]cyclohepten-5-ylidene)-ethylsulfanyl]-2-methylphenoxy}-acetic acid

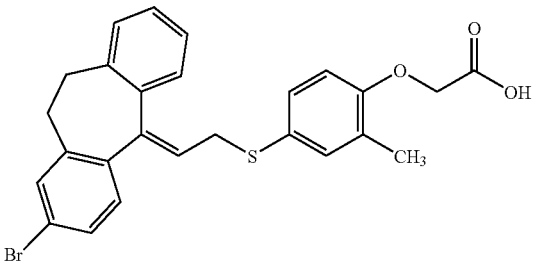

A mixture of 3-bromotoluene (42.8 g, 0.25 mol), N-bromosuccinimide (48.9 g, 0.275 mol) and benzoyl peroxide (0.75 g) in tetrachloromethane (500 mL) was stirred and heated to reflux for 3 h. The mixture was left to stand overnight at laboratory temperature, the solid was filtered off, washed with tetrachloromethane and the filtrates were evaporated. The residue was distilled in vacuo to yield 52.7 g (62.5%) of 1-bromo-3-bromomethylbenzene, b.p. 135-140° C./1.6 kPa.

The above bromide (52.7 g, 0.21 mol) was warmed up to 120° C. and then triethyl phosphite (35.0 g, 36.7 mL, 0.21 mol) was added dropwise under stirring. The temperature was increased to 150° C., the mixture was stirred for 6 h and left to stand overnight at room temperature. The residue was distilled to give 61.55 g (95.5%) of (3-bromobenzyl)phosphonic acid diethyl ester, b.p. 124-126° C./13 Pa.

Sodium (6.9 g, 0.3 mol) was melted in argon atmosphere on oil bath (130° C.). Methanol (10.1 g, 12.75 mL, 0.315 mol) was added dropwise under slow stirring with mechanical stirrer at 140-150° C. during 30 min. Pulverous sodium methoxide was heated at 140° C. for next 30 min, cooled down to 20° C. and dimethylformamide (30 mL) was added. The mixture was cooled to 5° C. and then a solution of above phosphonic ester (36.9 g, 0.12 mol) and phtalaldehydic acid (18.0 g, 0.12 mol) in dimethylformamide (30 mL) was added dropwise under cooling during 10 min (temperature was maintained between 10-20° C.). The reaction mixture was stirred for next 30 min at room temperature, cooled to 5° C., the mixture of conc. hydrochloric acid (20 mL) and water (150 mL) were added dropwise and the product was extracted with chloroform (100 mL, 2×30 mL). The combined organic solution were washed with water (2×80 mL) and evaporated in vacuo. The residue was stirred with water (350 mL) for 2 h, solid was filtered, washed with water (500 mL) and dried. This afforded 32.6 g (90%) of crude 2-[2-(3-bromo-phenyl)-vinyl]-benzoic acid, m.p. 145-150° C.

$R_F$ 0.75 ($SiO_2$, ethyl acetate/ethanol/acetic acid 60:40:1).

The above acid (15.0 g, 0.05 mol) was dissolved 15% ammonium hydroxide (100 mL) at 50° C. A charcoal (2 g) was added, the mixture was stirred for 30 min, filtered and clear solution was evaporated in vacuo. The residue was dissolved in water (100 mL), rhodium on activated charcoal (5%, 1.5 g) was added and the mixture was hydrogenated at 47° C. and 20-30 at for 15 min. Next portion of catalyst was added (1.3 g) and hydrogenation was continued for next 15 min (the same conditions). The catalyst was filtered off, the filtrate was acidified to pH 2 with conc. hydrochloric acid and product was extracted with chloroform (3×50 mL). Combined extracts were washed with water, dried ($MgSO_4$) and evaporated in vacuo and the residue was submitted to chromatography on the column of silica gel (Fluka 60,100 g). Elution with the mixture of hexane/ethyl acetate gave 10.8 g (71%) of 2-[2-(3-bromophenyl)ethyl]benzoic acid, m.p. 88-90° C.

$R_F$ 0.65 ($SiO_2$, hexane/ethyl acetate 6:4).

$^1$H NMR spectrum (250 MHz, $CDCl_3$): 8.15 (m, 1 H); 7.48-7.11 m, 7 H); 3.32 (t, J=7.7 Hz, 2 H); 3.32 (t, J=7.7 Hz, 2 H).

Elution with the mixture of hexane/ethyl acetate 1:1 afforded 2.85 g of 2-[2-(3-phenyl)ethyl]-benzoic acid, m.p. 138-139° C. as a by-product.

$R_F$ 0.50 ($SiO_2$, hexane/ethyl acetate 6:4).

To a stirred mixture of the above acid (9.5 g, 0.031 mol) and dimethylformamide (0.5 g) in dichloromethane (180 mL) oxalyl chloride (2.7 mL, 0.0374 mol) was added dropwise during 30 min. The mixture was stirred for next 30 min at mom temperature and then evaporated in vacuo. The residue was dissolved in the mixture of dichloromethane (150 mL) and carbon disulphide (50 mL) and to this solution aluminium chloride (6.4 g, 0.048 mol) was added portionwise and the reaction mixture was stirred overnight. The mixture was poured in crushed ice, 15% hydrochloric acid (60 mL) was added and product was extracted with dichloromethane (150, 2×80 mL). The collected organic solutions were washed with water (80 mL), 10% solution of sodium carbonate (50 mL), dried ($MgSO_4$) and evaporated. The residue (8.1 g) was purified by chromatography on a column of silica gel (Fluka 60, 100 g, hexane/benzene 8:2). This afforded 3.8 g (43%) of 2-bromo-10,11-dihydro-dibenzo[a,d]cyclohepten-5-one, m.p. 94-96° C.

$R_F$ 0.55 ($SiO_2$, hexane/benzene 1:1).

$^1$H NMR spectrum (250 MHz, $CDCl_3$): 8.00 (d, 1 H); 7.91 (d, 1 H); 7.88-7.21 (m, 5 H); 3.08 (s, 4 H).

For $C_{15}H_{11}BrO$

Calculated: C, 62.74%; H, 3.86%; Br, 27.83%.

Found: C, 63.12%; H, 3.86%; Br, 27.33%.

Magnesium turnings (0.234 g, 9.7 mmol) under tetrahydrofuran (3 mL) was activated with grain of iodine and with 1,2-dibromoethane (0.15 mL) and after the reaction was over, a solution of vinylbromide (1.04 g, 9.7 mmol) in tetrahydrofuran (18 mL) was added (dry ice condenser, nitrogen atmosphere). The reaction start immediately and the remaining part of the vinyl bromide solution was added dropwise under stirring at such a rate as to maintain the mixture under reflux (30 min). The mixture was stirred at 65° C. for next 30 min, cooled to 35° C. and then over 25 min a solution of the above ketone (1.39 g, 4.84 mmol) in tetrahydrofuran (25 mL) was added dropwise. The mixture was stirred at 35° C. for 3 h and then poured on a mixture of crushed ice (50 g) and 25% solution of ammonium chloride (10 mL). The mixture was extracted with diethyl ether (50 mL, 2×20 mL), combined organic solutions were washed with brine, dried ($MgSO_4$) and evaporated in vacuo. The residue (1.8 g) was purified by flash-chromatography on silica gel (Fluka 60, 80 g, hexane/benzene 6:4) to yield 1.15 g (75%) of 2-bromo-5-vinyl-10,11-dihydro-5H-dibenzo[a,d]cyclohepten-5-ol.

$R_F$ 0.40 ($SiO_2$, hexane/benzene 6:4).

$^1$H NMR spectrum (250 MHz, $CDCl_3$): 7.92 (m, 1 H); 7.78 (d, 1 H); 7.36-7.12 (m, 5 H); 6.31 (dd, 1 H); 5.24 (d, 1 H); 4.90 (d, 1 H); 3.42 (m, 2 H). 2.86 (m, 2 H); 2.24 (s, 1 H).

A suspension of the above alcohol (1.1 g, 3.49 mmol) in acetic acid (10 mL) was stirred and treated at 15° C. with 15% solution of hydrogen bromide in acetic acid (7 mL) over 15 min. The mixture was stirred at 15° C. for 30 min and then at laboratory temperature for 1.5 h and evaporated in vacuo. The rest of acetic acid was removed by addition of 40 mL xylene and evaporation in vacuo and the residue was chromatographed in a short column of silica gel Fluka 60 (50 g, benzene). The benzene solutions were evaporated in vacuo to yield 1.25 g (95%) of 2-bromo-5-(2-bromo-ethylidene)-10,11-dihydro-5H-dibenzo[a,d]cycloheptene.

$R_F$ 0.85 ($SiO_2$, hexane/benzene 8:2).

$^1$H NMR spectrum (250 MHz, $CDCl_3$): 7.36-7.08 (m, ~7 H); 6.16 (q, J=8.5 Hz, 1 H); 4.00 (m, 2 H); 3.35 (m, 2 H); 2.95 (m, 2 H).

General Procedure (A)

Step B:

The mixture of above bromide (1.15 g, 3.86 mmol), (4-mercapto-2-methylphenoxy)acetic add ethyl ester (1.11 g, 4.24 mmol), potassium carbonate (1.06 g, 7.7 mmol) and cesium carbonate (0.1 g) in tetrahydrofuran (15 mL) was stirred at 70-80° C. for 20 h. The solid was filtered off, washed with tetrahydrofuran and the filtrates were evaporated in vacuo. The residue was purified by flash-chromatography on silica gel (Fluka 60, 75 g, hexane/ethyl acetate 95:5) to yield 0.49 g (24%) of {4-[2-(2-bromo-10,11-dihydro-dibenzo[a,d] cyclohepten-5-ylidene)-ethylsulfanyl]-2-methyl-phenoxy}-acetic acid ethyl ester as an oil.

$R_F$ ($SiO_2$, chloroform/methanol 4:1) 0.35.

$^1$H NMR spectrum (250 MHz, $CDCl_3$): 7.30-7.06 (m, 10 H); (6.54 (m, 1 H); 5.94 (m, 1 H); 4.61 (s, 2 H); 4.28 (q, J=7.2 Hz, 2 H); 3.40-2.65 (unresolv. m, ~2 H); 2.95 (m, 2 H); 2.21 (s, 3 H); 1.29 (t, J=7.2 Hz, 3 H).

General Procedure (B)
Step A:

A 2 M solution of lithium hydroxide (0.47 mL, 1.12 mmol) was added to a solution of the above ester (0.44 g, 0.84 mmol) in tetrahydrofuran (15 mL) and ethanol (30 mL) and the resulting mixture was stirred at ambient temperature 3 h. The solution was evaporated in vacuo, the residue was diluted with water (20 mL), acidified with 2M tartaric acid to pH~3 and the mixture was extracted with dichloromethane (3×15 mL). The collected organic extracts were washed with water (10 mL), brine (10 mL) dried with anhydrous magnesium sulfate and evaporated in vacuo. The residue was purified by column chromatography (silica gel Fluka 60, chloroform/methanol 7:1), giving the title compound (160 mg, 41%).

$R_F$ 0.25 (SiO$_2$, chloroform/methanol 8:2).

$^1$H-NMR spectrum (250 MHz, CDCl$_3$): 7.12-6.85 (m, ~9 H); 6.66 (m, 1 H); 5.87 (m, 1H); 4.42 (s, 2 H); 3.55-2.55 (m, Σ 6 H); 2.11 (s, 3 H).

The above acid (150 mg, 0.3 mmol) and L-lysine (44 mg, 0.3 mmol) were dissolved in a mixture of dichloromethane (5 mL), acetone (20 mL), methanol (20 mL) and water (5 drops). The reaction mixture was stirred at ambient temperature for 2 h and subsequently evaporated to dryness. The residue was repeatedly triturated with dry diethyl ether (5×25 mL) and the residue after the last decantation was dried in vacuo giving the L-lysine salt of the title acid as a amorphous solid.

Yield: 43 mg (22%).

Example 2

{4-[2-(2-Phenyl-10,11-dihydro-dibenzo[a,d]cyclo-hepten-5-ylidene)-ethylsulfanyl]-2-methylphenoxy}-acetic acid

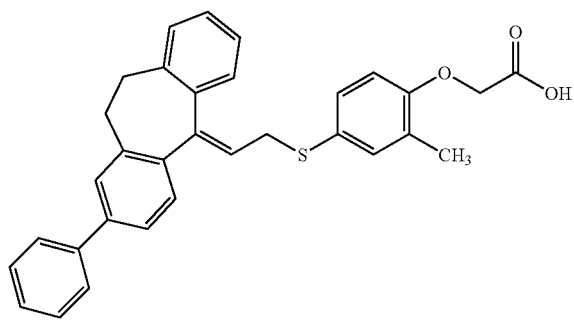

Tetrakis(triphenylphosphine)palladium (0.22 g, 0.19 mmol) was added in argon atmosphere to a mixture of 2-bromo-10,11-dihydro-dibenzo[a,d]cyclohepten-5-one (1.72 g, 6 mmol; prepared as described in example 1), phenylboronic acid (0.8 g, 6.6 mmol) and 2M sodium carbonate solution (6 mL, 12 mmol) in toluene (15 mL) and ethanol (15 mL). The mixture was refluxed for 2.5 h. The reaction mixture was diluted with water (50 mL) and extracted with diethyl ether (50 mL, 2×30 mL). The combined ethereal solutions were washed with water (50 mL), brine (50 mL), dried (MgSO$_4$) and evaporated in vacuo give an oil (2.8 g). The oil was chromatographed on silica gel (Fluka 60, 80 g) eluting with the mixture of hexane/benzene 1:1 to give 1.52 g (89%) of 2-phenyl-10,11-dihydro-dibenzo[a,d]cyclohepten-5-one.

$R_F$ 0.55 (SiO$_2$, hexane/benzene 1:1).

$^1$H NMR spectrum (250 MHz, CDCl$_3$): 8.14 (d, 1 H); 8.02 (d, 1 H); 7.63-7.23 (m, 10 H); 3.25 (m, 4 H).

Magnesium turnings (0.45 g, 18.5 mmol) under tetrahydrofuran (5 mL) was activated with grain of iodine and with 1,2-dibromoethane (0.25 mL) and after the reaction was over, a solution of vinyl bromide (2.0 g, 18.5 mmol) in tetrahydrofuran (30 mL) was added (dry ice condenser, nitrogen atmosphere). The reaction start immediately and the remaining part of the vinyl bromide solution was added dropwise under stirring at such a rate as to maintain the mixture under reflux (30 min). The mixture was stirred at 65° C. for next 30 min, cooled to 35° C. and then over 30 min a solution of the above ketone (1.75 g, 6.15 mmol) in tetrahydrofuran (35 mL) was added dropwise. The mixture was stirred at 35° C. for 3 h and then poured on a mixture of crushed ice (100 g) and 25% solution of ammonium chloride (30 mL). The mixture was extracted with diethyl ether (50 mL, 2×20 mL), combined organic solutions were washed with brine, dried (MgSO$_4$) and evaporated in vacuo. The residue (2.5 g) was purified by flash-chromatography on silica gel (Fluka 60, 80 g, hexane/benzene 6:4) to yield 1.65 g (86%) of 2-phenyl-5-vinyl-10,11-dihydro-5H-dibenzo[a,d]cyclohepten-5-ol.

$R_F$ 0.35 (SiO$_2$, hexane/benzene 6:4).

$^1$H NMR spectrum (250 MHz, CDCl$_3$): 7.92 (m, 1 H); 7.79 (m, 2 H); 7.59-7.16 (m, 10 H); 6.38 (dd, 1 H); 5.25 (d, 1 H); 4.96 (d, 1 H); 3.49 (m, 2 H). 2.97 (m, 2 H); 2.28 (s, 1 H).

A suspension of the above alcohol (1.56 g, 5.06 mmol) in acetic acid (15 mL) was stirred and treated at 15° C. with 15% solution of hydrogen bromide in acetic acid (10 mL) over 15 min. The mixture was stirred at 15° C. for 30 min and then at laboratory temperature for 1.5 h and evaporated in vacuo. The rest of acetic acid was removed by addition of 40 mL xylene and evaporation in vacuo and the residue was chromatographed in a short column of silica gel Fluka 60 (75 g, benzene). The benzene solutions were evaporated in vacuo to yield 1.58 g (87.5%) of 2-phenyl-5-(2-bromo-ethylidene)-10,11-dihydro-5H-dibenzo[a,d]cycloheptene.

$R_F$ 0.85 (SiO$_2$, hexane/benzene 82).

$^1$H NMR spectrum (250 MHz, CDCl$_3$): 7.4-7.06 (m, ~12 H); 6.23 (q, J=8.5 Hz, 1 H); 4.05 (m, 2 H); 3.35 (m, 2 H); 2.95 (m, 2 H).

General Procedure (A)
Step B:

The mixture of above bromide (0.95 g, 2.65 mmol), (4-mercapto-2-methylphenoxy)acetic acid ethyl ester (0.565 g, 2.65 mmol), potassium carbonate (0.733 g, 5.30 mmol) and cesium carbonate (0.1 g) in 2-butanone (15 mL) was stirred at 70-80° C. for 24 h. The solid was filtered off, washed with 2-butanone and the filtrates were evaporated in vacuo. The residue was purified by flash-chromatography on silica gel (Fluka 60, 75 g, hexane/ethyl acetate 95:5) to yield 0.39 g (28%) of {4-[2-(2-phenyl-10,11-dihydro-dibenzo[a,d]cyclohepten-5-ylidene)-ethylsulfanyl]-2-methyl-phenoxy}-acetic acid ethyl ester as an oil.

$R_{F\ (SiO2)}$, hexane/ethyl acetate 9:1) 0.40.

$^1$H NMR spectrum (250 MHz, CDCl$_3$): 7.58-7.03 (m, ~14 H); 6.58 (m, 1 H); 5.99 (m, 1 H); 4.60 (s, 2 H); 4.28 (q, 2 H); 3.75-2.60 (unresolv. m, ~4 H); 2.21 (s, 3 H); 1.29 (t, 3 H).

General Procedure (B)
Step A:

A 2 M solution of lithium hydroxide (0.36 mL, 0.72 mmol) was added to a solution of the above ester (0.34 g, 0.653 mmol) in tetrahydrofuran (12 mL) and ethanol (25 mL) and the resulting mixture was stirred at ambient temperature 3 h. The solution was evaporated in vacuo, the residue was diluted with water (20 mL), acidified with 2M tartaric acid to pH~3 and the mixture was extracted with dichloromethane (3×15 mL). The collected organic extracts were washed with water (10 mL), brine (10 mL) dried with anhydrous magnesium sulfate and evaporated in vacuo. The residue was purified by column chromatography (silica gel Fluka 60, chloroform/methanol 7:1), giving the title compound (130 mg, 40.5%).

$R_F$ 0.25 ($SiO_2$, $CHCl_3$/MeOH 8:2).

$^1$H-NMR spectrum (250 MHz, $CDCl_3$): 7.45-6.82 m, 14 H, 6.65 d, 1 H, 5.88 q, 1 H, 4.43 s, 2 H, 3.75-2.85 bm, ~4 H, 2.22 s, 3 H.

The above acid (100 mg, 0.2 mmol) and L-lysine (30 mg, 0.2 mmol) were dissolved in a mixture of acetone (15 mL), methanol (20 mL) and water (5 mL). The reaction mixture was stirred at ambient temperature for 2 h and subsequently evaporated to dryness. The residue was repeatedly triturated with dry diethyl ether (5×25 mL) and the residue after the last decantation was dried in vacuo giving the L-lysine salt of the title acid as a amorphous solid.

Yield: 76 mg (59.5%).

Pharmacological Methods

In Vitro PPARalpha, PPARgamma and PPARdelta Activation Activity

The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50-80% at transfection. A total of 0.8 µg DNA containing 0.64 µg pM1α/γLBD, 0.1 µg pCMVβGal, 0.08 µg pGL2(Gal4)$_5$ and 0.02 µg pADVANTAGE was transfected per well using FuGene transfection reagent according to the manufacturers instructions (Roche). Cells were allowed to express protein for 48 h followed by addition of compound.

Plasmids: Human PPAR α, γ and δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARα: aa 167-C-terminus; PPARγ: aa 165-C-terminus; PPARδ: aa 128-C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAG-TACTGTCCTCCG(AG)) (Webster et al. (1988), Nucleic Acids Res. 16, 8192) into the vector pGL2 promoter (Promega) generating the plasmid pGL2(GAL4)$_5$. pCMVβ-Gal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments.

Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 µl supernatant from each transfection lysate was transferred to a new microplate. β-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as mean±SD.

The invention claimed is:

1. A compound of formula (I) or a pharmaceutically acceptable salt thereof:

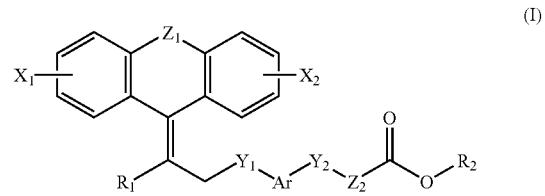

wherein $X_1$ is hydrogen, halogen, hydroxy, cyano, or amino; or $X_1$ is $C_{1-6}$-alkyl, $C_{3-6}$-cycloalkyl, $C_{2-6}$-alkenyl, $C_{2-6}$-alkynyl, aralkyl, heteroaralkyl, aryl$C_{2-6}$-alkynyl, heteroaryl$C_{2-6}$-alkynyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; or $X_1$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens;

$X_2$ is hydrogen, halogen, hydroxy, cyano, or amino; or $X_2$ is $C_{1-6}$-alkyl, $C_{3-6}$-cycloalkyl, $C_{2-6}$-alkenyl, $C_{2-6}$-alkynyl, aralkyl, heteroaralkyl, aryl$C_{2-6}$-alkynyl, heteroaryl$C_{2-6}$-alkynyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; or $X_2$ is aryl or heteroaryl each of which is optionally substituted with one or more substituents, where said substituents independently are:

halogen, hydroxy, cyano, amino or carboxy; or $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens;

Ar is arylene which is optionally substituted with one or more substituents, where said substituents independently are:

halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or two of the substituents when placed in adjacent positions together with the atoms to which they are attached my form a five to eight member ring;

$Y_1$ is O or S;

$Y_2$ is O or S;

$Z_1$ is —$(CH_2)_n$— wherein n is 0, 1, 2 or 3;

$Z_2$ is —$(CH_2)_m$— wherein m is 1, 2 or 3;

$R_1$ is hydrogen, halogen or $R_1$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and $R_2$ is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl.

2. The compound according to claim 1, wherein $X_1$ is halogen or cyano.

3. The compound according to claim 1, wherein $X_1$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens.

4. The compound according to claim 3, wherein $X_1$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, arylcarbonyl, $C_{1-6}$-alkylsulfonyl, $C_{1-6}$-alkylsulfonyloxy, arylsulfonyl, arylsulfonyloxy each of which is optionally substituted with one or more halogens.

5. The compound according to claim 4, wherein $X_1$ is $C_{1-6}$-alkyl, aralkyl, heteroaralkyl, $C_{1-6}$-alkoxy, $C_{3-6}$-cycloalkoxy, aryloxy, aralkoxy, heteroaralkoxy, each of which is optionally substituted with one or more halogens.

6. The compound according to claim 5, wherein $X_1$ is $C_{1-6}$-alkyl or $C_{1-6}$-alkoxy, each of which is optionally substituted with one or more halogens.

7. The compound according to claim 1, wherein $X_1$ is aryl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

8. The compound according to claim 7, wherein $X_1$ is aryl optionally substituted with one or more substituents, where said substituents independently are:

halogen; or $C_{1-6}$-alkyl optionally substituted with one or more halogens.

9. The compound according to claim 8, wherein $X_1$ is aryl optionally substituted with one or more halogens.

10. The compound according to any one of the claim 9, wherein $X_1$ is phenyl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

11. The compound according to claim 10, wherein $X_1$ is phenyl optionally substituted with one or more substituents, where said substituents independently are:

halogen; or $C_{1-6}$-alkyl optionally substituted with one or more halogens.

12. The compound according to claim 11, wherein $X_1$ is phenyl optionally substituted with one or more halogens.

13. The compound according to claim 1, wherein $X_1$ is heteroaryl optionally substituted with one or more substituents, where said substituents independently are:

halogen; or $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

14. The compound according to claim 13, wherein $X_1$ is heteroaryl optionally substituted with one or more substituents, where said substituents independently are:

halogen; or $C_{1-6}$-alkyl optionally substituted with one or more halogens.

15. The compound according to claim 14, wherein $X_1$ is heteroaryl optionally substituted with one or more halogens.

16. The compound according to any one of the claim 15, wherein $X_1$ is furyl or thienyl optionally substituted with one or more halogens.

17. The compound according to claim 16, wherein $X_2$ is halogen or cyano.

18. The compound according to claim 16, wherein $X_2$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, $C_{1-6}$-alkylsulfonyloxy, arylsulfonyl, arylsulfonyloxy, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens.

19. The compound according to claim 18, wherein $X_2$ is $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, arylcarbonyl, $C_{1-6}$-alkylsulfonyl, $C_{1-6}$-alkylsulfonyloxy, arylsulfonyl, arylsulfonyloxy each of which is optionally substituted with one or more halogens.

20. The compound according to claim 19, wherein $X_2$ is $C_{1-6}$-alkyl, aralkyl, heteroaralkyl, $C_{1-6}$-alkoxy, $C_{3-6}$-cycloalkoxy, aryloxy, aralkoxy, heteroaralkoxy, each of which is optionally substituted with one or more halogens.

21. The compound according to claim 20, wherein $X_2$ is $C_{1-6}$-alkyl or $C_{1-6}$-alkoxy, each of which is optionally substituted with one or more halogens.

22. The compound according to claim 16 wherein $X_2$ is aryl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

23. The compound according to claim 22, wherein $X_2$ is aryl optionally substituted with one or more substituents, where said substituents independently are:
  halogen; or
  $C_{1-6}$-alkyl optionally substituted with one or more halogens.

24. The compound according to claim 23, wherein $X_2$ is aryl optionally substituted with one or more halogens.

25. The compound according to claim 24, wherein $X_2$ is phenyl optionally substituted with one or more substituents, where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

26. The compound according to claim 25, wherein $X_2$ is phenyl optionally substituted with one or more substituents where said substituents independently are:
  halogen; or
  $C_{1-6}$-alkyl optionally substituted with one or more halogens.

27. The compound according to claim 26, wherein $X_2$ is phenyl optionally substituted with one or more halogens.

28. The compound according to claim 16, wherein $X_2$ is heteroaryl optionally substituted with one or more substituents where said substituents independently are:
  halogen; or
  $C_{1-6}$-alkyl, $C_{1-6}$-alkoxy, $C_{1-6}$-alkylsulfonyl or $C_{1-6}$-alkylsulfonyloxy each of which is optionally substituted with one or more halogens.

29. The compound according to claim 28, wherein $X_2$ is heteroaryl optionally substituted with one or more substituents where said substituents independently are:
  halogen; or
  $C_{1-6}$-alkyl optionally substituted with one or more halogens.

30. The compound according to claim 29, wherein $X_2$ is heteroaryl optionally substituted with one or more halogens.

31. The compound according to claim 30, wherein $X_2$ is furyl or thienyl optionally substituted with one or more halogens.

32. The compound according to claim 31, wherein Ar is phenylene which is optionally substituted with one or more substituents, where said substituents independently are:
  halogen, hydroxy or cyano; or
  $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or
  two of the substituents when placed in adjacent positions together with the atoms to which they are attached my form a five to eight member ring.

33. The compound according to claim 32, wherein Ar is phenylene which is optionally substituted with one or more substituents, where said substituents independently are:
  halogen; or
  $C_{1-6}$-alkyl, $C_{1-6}$-alkoxy, aryloxy or aralkoxy each of which is optionally substituted with one or more halogens; or
  two of the substituents when placed in adjacent positions together with the atoms to which they are attached form a five membered ring.

34. The compound according to claim 33, wherein Ar is phenylene which is optionally substituted with methyl.

35. The compound according to claim 34, wherein Ar is phenylene.

36. The compound according to claim 35, wherein $Y_1$ is S.

37. The compound according to claim 36, wherein $Y_2$ is O.

38. The compound according to claim 37, wherein n is 1 or 2.

39. The compound according to claim 38, wherein m is 1.

40. The compound according to claim 39, wherein $R_1$ is hydrogen or $R_1$ is $C_{1-6}$-alkyl, aralkyl, $C_{1-6}$-alkoxy, aryloxy, aralkoxy each of which is optionally substituted with one or more halogens.

41. The compound according to claim 40, wherein $R_1$ is hydrogen or $R_1$ is $C_{1-6}$-alkyl, $C_{1-6}$-alkoxy each of which is optionally substituted with one or more halogens.

42. The compound according to claim 41, wherein $R_1$ is hydrogen.

43. The compound according to claim 42, wherein $R_2$ is hydrogen.

44. The compound according to claim 1, where the compound is a compound selected from the group consisting of:
  {4-[2-(2-Bromo-10,11-dihydro-dibenzo[a,d]cyclohepten-5-ylidene)-ethylsulfanyl]-2-methyl-phenoxy}-acetic acid; and
  {4-[2-(2-Phenyl-10,11-dihydro-dibenzo[a,d]cyclohepten-5-ylidene)-ethylsulfanyl]-2-methyl-phenoxy}-acetic acid;
  or a pharmaceutically acceptable salt thereof.

45. The compound according to claim 1, which is a PPARδ agonist.

46. The compound according to claim 45, which is a selective PPARδ agonist.

47. A pharmaceutical composition comprising a compound of claim 1 and a pharmaceutically acceptable carrier or excipient.

48. The pharmaceutical composition according to claim 47 in unit dosage form, comprising from 0.05 mg to 1000 mg, or from 0.1 to 500 mg, or from 0.5 mg to 200 mg of the compound.

49. A method of treating a disease, disorder, or condition comprising administering to a subject a compound according to claim 1, where the disease, disorder, or condition is selected from the group consisting of type 1 diabetes, type 2 diabetes, dyslipidemia, syndrome X, metabolic syndrome, impaired glucose tolerance, insulin resistance, hypertrigyceridaemia, obesity, cardiovascular diseases, atherosclerosis, and hypercholesteremia.

* * * * *

UNITED STATES PATENT AND TRADEMARK OFFICE
CERTIFICATE OF CORRECTION

PATENT NO. : 8,053,598 B2  
APPLICATION NO. : 11/579717  
DATED : November 8, 2011  
INVENTOR(S) : Zdenek Polivka Page 1 of 1

It is certified that error appears in the above-identified patent and that said Letters Patent is hereby corrected as shown below:

In column 27, line 40, in claim 1, delete "my" and insert -- may --, therefor.

In column 28, line 28, in claim 10, after "according to" delete "any one of the".

In column 28, line 58, in claim 16, after "according to" delete "any one of the".

In column 30, line 9, in claim 32, delete "my" and insert -- may --, therefor.

In column 30, line 63-64, in claim 49, delete "hypertrigyceridaemia," and insert -- hypertriglyceridemia, --, therefor.

In column 30, line 65, in claim 49, delete "hypercholesteremia." and insert -- hypercholesterolemia. --, therefor.

Signed and Sealed this
Twenty-seventh Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,053,598 B2 | Page 1 of 1 |
| APPLICATION NO. | : 11/579717 | |
| DATED | : November 8, 2011 | |
| INVENTOR(S) | : Polivka | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 660 days.

Signed and Sealed this
Thirty-first Day of January, 2012

David J. Kappos
*Director of the United States Patent and Trademark Office*